United States Patent [19]

Piché et al.

[11] Patent Number: 5,408,881
[45] Date of Patent: Apr. 25, 1995

[54] HIGH RESOLUTION ULTRASONIC INTERFEROMETRY FOR QUANTITATIVE MONDESTRUCTIVE CHARACTERIZATION OF INTERFACIAL ADHESION IN MULTILAYER COMPOSITES

[75] Inventors: Luc Piché, Montreal; Daniel Lévesque, Terrebonne, both of Canada

[73] Assignee: National Research Council of Canada, Ottawa, Canada

[21] Appl. No.: 121,367

[22] Filed: Sep. 15, 1993

[51] Int. Cl.⁶ ............................................. G01N 29/04
[52] U.S. Cl. ........................................ 73/582; 73/588
[58] Field of Search ................. 73/602, 599, 579, 582, 73/588

[56] References Cited

U.S. PATENT DOCUMENTS

| | | | |
|---|---|---|---|
| 3,996,791 | 12/1976 | Niklas | 73/602 |
| 4,545,250 | 10/1985 | Miwa | 73/602 |
| 5,118,464 | 6/1992 | Richardson, Jr. | 73/592 |
| 5,152,401 | 10/1992 | Affeldt, Jr. | 73/579 |
| 5,303,590 | 4/1994 | Modderman | 73/588 |
| 5,305,239 | 4/1994 | Kinra | 73/603 |

FOREIGN PATENT DOCUMENTS 61-254850 11/1986 Japan ................................ 73/602

OTHER PUBLICATIONS

Yee, B. G. W. et al. "Applications of Ultrasonic Interference Spectroscopy of Materials and Flow Characterization." *Materials Evaluation*, (Aug. 1975), pp. 193–202.
Chang, F. H., et al. "Transmission Frequency Spectra of Ultrasonic Waves through Multi-Layer Media." 1973 Ultrasonic Symposium Proceedings, (Nov. 5–7, 1973) pp. 209–215.
Allen, D. R., et al. "A Fourier Transform Technique that Measures Phase Delays between Ultrasonic Impulses with Sufficient Accuracy to Determine Residual Stresses in Metals". *NDT International*, vol. 16, No. 4 (Aug. 1983), pp. 205–217.

*Primary Examiner*—Hezron E. Williams
*Assistant Examiner*—Christine K. Oda
*Attorney, Agent, or Firm*—Neil Teitelbaum

[57] ABSTRACT

An ultrasonic interferometry technique for composite structures such as metal/polymer/metal structures exhibits high sensitivity to interfacial properties, even at usual ultrasonic wavelengths. A model for the ultrasonic response of multilayered media accounts for viscoelasticity. Results of numerical calculations point out scaling features for interfacial properties in terms of specific stiffness S. A method is provided for characterizing the interfacial adhesion in a multilayer composite in terms of the parameter S. The multilayer composite is ultrasonically irradiated with a pulsed signal to obtain a signal characteristic of the interfacial adhesion between the multilayers. A model is provided of the multilayer composite that includes at least two additional layers which model the behaviour of the interface between the composite layers. From the model, given various input parameters such as thickness of the two additional layers and the viscoelastic properties of the layers, a plurality of spectra, characteristic of interfacial adhesion between the modeled multilayer composite are obtained. The spectrum related to the ultrasonic signal is compared to the plurality of the modeled spectra and a best fit or match is obtained. The value of S relating to the best fit model is determined to be the value which characterizes the interfacial adhesion between layers of the irradiated composite.

5 Claims, 10 Drawing Sheets

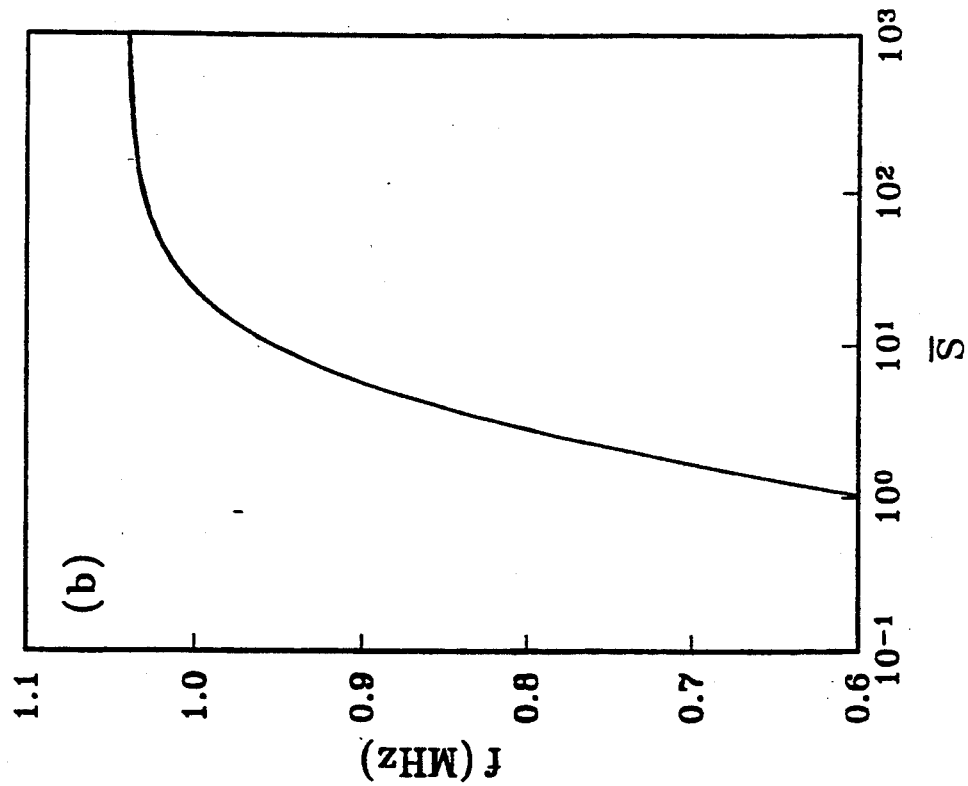
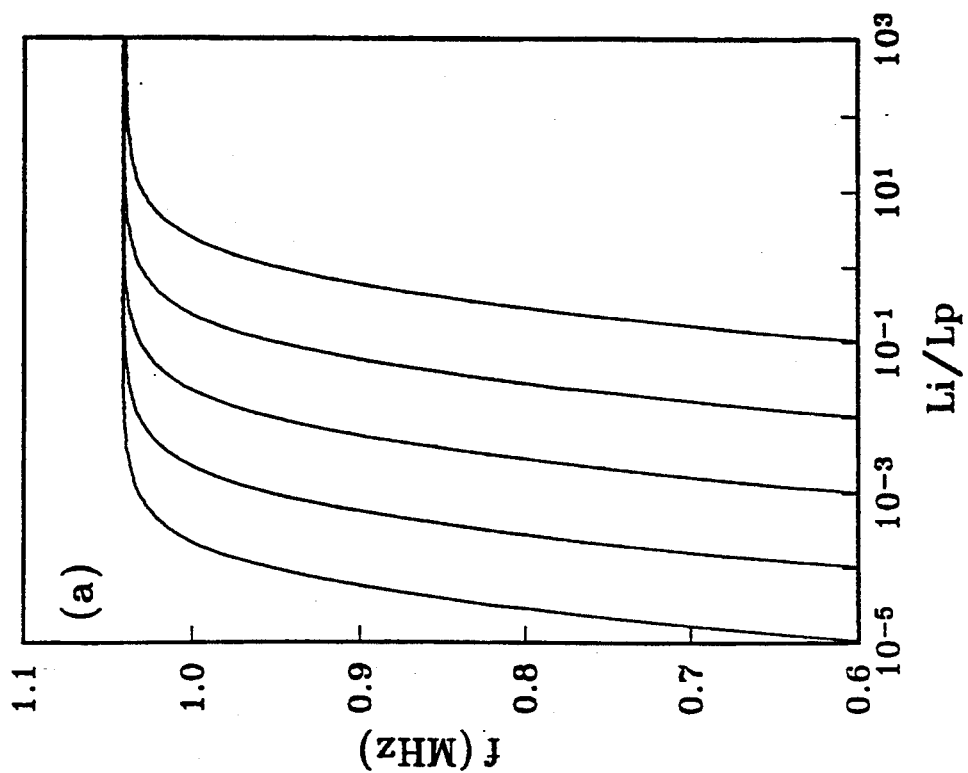
Fig. 3a
Fig. 3b

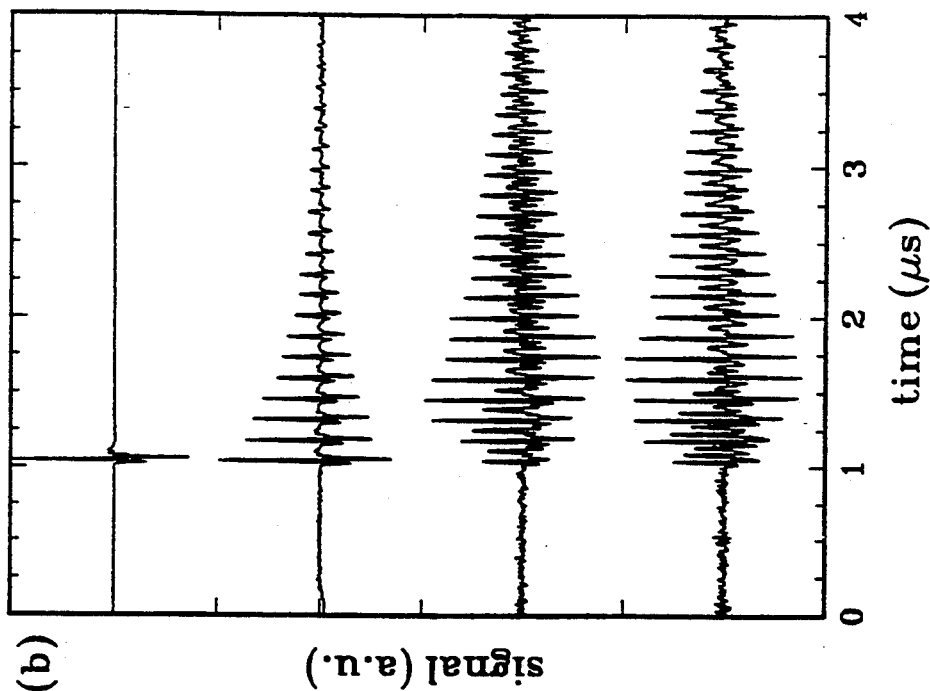
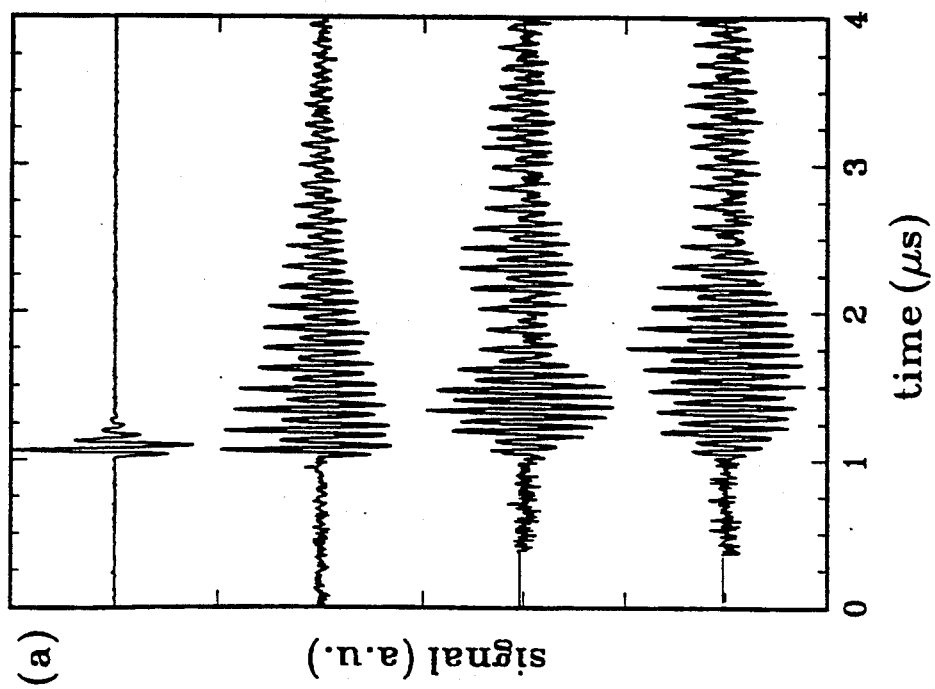
Fig. 7a
Fig. 7b

HIGH RESOLUTION ULTRASONIC INTERFEROMETRY FOR QUANTITATIVE MONDESTRUCTIVE CHARACTERIZATION OF INTERFACIAL ADHESION IN MULTILAYER COMPOSITES

FIELD OF THE INVENTION

This invention relates generally to an ultrasonic method for the quantitative and nondestructive characterization of interfacial adhesion, and more particularly to adhesion between at least 3 layers of a multilayer structure.

BACKGROUND OF THE INVENTION

Polymer based composites often serve as a substitute for traditional industrial materials; these composites are relatively easy to fabricate and are becoming ubiquitous in the materials industry. An increased use of polymer based composites designed for specific uses has stimulated theoretical efforts oriented at describing and modeling their properties. Models often rely on information concerning boundary conditions for continuity of displacement and stress between the constituents of a composite and investigators generally assume rigid bonding as described by L. Piché (the applicant) and A. Hamel, in Polym. Compos. 7, 355, 1986; 8,22,1987. However, when polymers are involved, this description is incomplete and viscoelastic behavior must be accounted for. Bonding is never perfectly stiff (good bonding), nor perfectly soft (bad bonding); instead, one should make reference to a quantitative criterion related to materials properties.

Recently, a great deal of progress has been made in understanding the physical structure and properties of polymer surfaces and interfaces. On one hand, efforts have been devoted to theoretical modeling either through analytical work or numerical simulations. On the other hand, new techniques provide density profiles with finer spatial resolution, such as Scanning Electron Microscopy (SEM, resolution 100 nm), Forward Recoil Spectroscopy (FRES, resolution 80 nm), Dynamic Secondary Mass Spectrometry (DSIMS, resolution 10 nm), Nuclear Reaction Analysis (NRA, resolution 10 nm), Small-Angle Neutron-Scattering (SANS, resolution 10 nm), Neutron Reflectivity (NR, resolution 1 nm), Transmission Electron Microscopy (TEM, resolution 1 nm), X-ray Photoelectron Spectroscopy (XPS, resolution 0.1 nm), in addition to more indirect means like Infrared Spectroscopy and Attenuated Total Reflectance Infrared Spectroscopy (ATR-IR, resolution 0.1 to 2 $\mu$m), or thermodynamic and hydrodynamic methods. Tools have also been developed that probe interfacial forces and complement traditional measurements. Newer methods include Scanning Tunneling Microscopy (STM), Atomic Force Microscopy (AFM), the quartz microbalance, and most relevant, the Surface Force Apparatus (SFA) that measures forces between surfaces as function of separation (resolution 0.1 nm) and between surfaces that confine fluids. Finally, techniques have been developed to study mobility near interfaces and to assess the dynamic properties of confined molecular systems.

These new methods, however, are not directly applicable to the characterization of adhesion in real structures because the interfaces are not accessible for measurements and because practical adhesion—for example, as measured in peel tests—relates to complex non-linear and non reversible processes that involve other materials characteristics. Notwithstanding, interfacial chemistry and interfacial interactions are essential factors in the making and breaking of bonds. Therefore, a nondestructive technique that correlates both to interfacial properties and irreversible mechanical behavior would be of great benefit.

Amongst the different approaches that have been investigated, namely nuclear magnetic resonance, acoustic emission, optical and thermal methods, ultrasonics have emerged as the most promising. Ultrasonic techniques have become more dependable for the detection and identification of defects due to lack of adhesive, delamination, porosity or surface roughness. However, it is only rather recently, that a significant amount of research has been devoted to the problem of interface adhesion per se.

It is an object of the invention, to provide a more reliable robust method for characterizing interfacial adhesion in a multilayer structure.

The invention provides an ultrasonic method that characterizes interfacial adhesion in terms of physical parameters. The method is based on analyzing the interferometric features associated with the reverberation of ultrasound in a multilayered system. The nature and the origin of interfacial adhesion is more clearly identified and a numerical scheme is presented for modeling the propagation of ultrasound in layered media; the invention provides a method for determining a simple materials constant which is an expression of interfacial adhesion in the form of a specific stiffness for the interfacial layer.

In accordance with the invention, a method is provided for characterizing the interfacial adhesion in a multilayer composite having at least three layers. The method comprises the steps of: irradiating the multilayer composite with a pulsed signal, each pulse having a width of about less than or equal to 100 ns to obtain a first signal characteristic of the interfacial adhesion between the multilayers; detecting a signal from the irradiated object; storing amplitude and phase information corresponding to the detected signal; convening the stored information from the time domain to the frequency domain to obtain a frequency spectrum related to the stored information; and, comparing the frequency spectrum with a spectrum derived from a model of a multilayer composite that includes at least two additional layers which model the behaviour of interface between the composite layers.

In accordance with the invention there is further provided, a method of characterizing the interfacial adhesion in a multilayer composite comprising the steps of:

a) ultrasonically irradiating the multilayer composite having at least 3 layers to obtain a first signal characteristic of the interfacial adhesion between the multilayers;

b) modeling the multilayer composite with a model that includes at least two additional layers which model the behaviour of the interface between the composite layers in such a manner as to obtain plurality of spectra, each spectrum being characteristic of interfacial adhesion between the modeled multilayer composite; and, c) comparing, in the frequency domain, a first signal characteristic of the interfacial adhesion between the multilayers with a plurality of the spectra obtained in step (b) to obtain a spectrum which most closely matches the spectrum of the first signal.

Advantageously, the invention provides a method of ultrasonically irradiating a composite, and for obtaining a measure in the form of a quantifiable index of the adhesion of the bond between the layers of the composite. The method not only allows a bond to be tested, but as well, it can be used as a tool so that bonds will meet specific desired levels of adhesion.

BRIEF DESCRIPTION OF THE DRAWINGS

Exemplary embodiments of the invention will now be described in conjunction with the drawings in which:

FIG. 3a is a numerical simulation graph of frequency peak positions versus modulus $L^*_i$, ($\tau = 500$ ns) of the interfacial layer with $d_i/d_p = 10^{-5}, 10^{-4} 10^{-3} 10^{-2} 10^{-1}$.

FIG. 3b is a graph of a reduced master curve of the data in FIG. 3a plotted against normalized specific stiffness, $\overline{S}_p = (d_p/L_p^*)(L_i^*/d_i)$;

FIG. 7a is a graph of amplitude versus time for 1) a reference signal in water alone, 2) a result from steel substrate in water, 3) a multilayer with anodized substrates and high adhesion, 4) a multilayer with cleansed only substrates and weak adhesion, all subjected to ultrasound;

FIG. 7b is a graph of amplitude versus time as in FIG. 7a however a different transducer pair is used;

DETAILED DESCRIPTION

Figure 1:
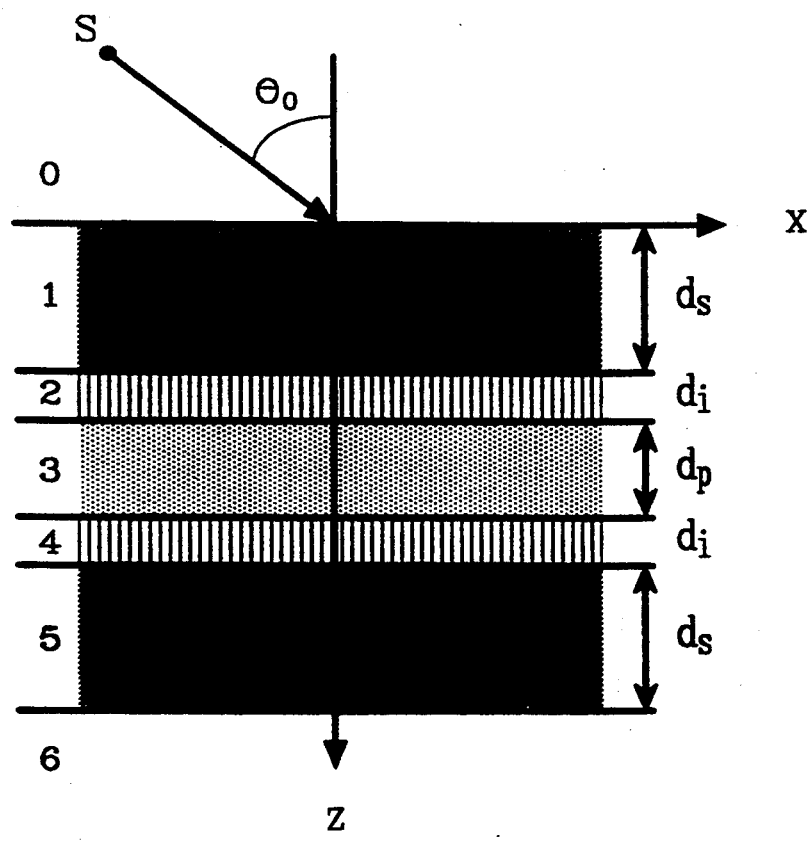
FIG. 1 is a cross-sectional view of a model of a three layer composite including two additional layers, of thickness $d_i$, representing adhesion between the three layers.

The word adhesion is commonly taken in a broad sense to describe the sticking together of materials. This invention, more specifically relates to layered composites, where two materials are bonded, "indirectly", through an intermediate layer of polymer adhesive. Structures of this kind have two interfaces that are prone to interfacial failure and three regions that are susceptible to cohesive failure; together these constitute complex situations. In the following description, adhesion will be considered with reference to bonding at the interface between two identical or dissimilar materials in intimate contact, and that are referred to as the adherend and the adhesive. More particularly, the adhesive behavior of thermoplastic polymers such as polypropylene(PP) will be discussed.

Polymers are comprised of molecules having N ($\approx 1000$ for PP) repeating units a length 1 ($\approx 0.3$ nm for PP), that are covalently linked in a chain like manner. Polymer adhesives are applied as melts, where the molecules form interpenetrated Gaussian coils with average radius $R_g \approx 1N^{\frac{1}{2}}$ ($\approx 10$ nm for PP). In these melts, intermolecular forces are associated with van der Waals interactions, and also with entanglements of the long chains. PP molecules exhibit strong intermolecular forces and a high degree of stereoregularity and upon cooling past the critical temperature for crystallization, $T_x (\approx 130°$ C. for PP), the chains may fold in an orderly way, forming crystalline lamellae dispersed in the melt. Finally, below the glass transition temperature $T_g$ ($\approx -40°$ C. for PP), the polymer becomes a glass where the random structure is frozen-in.

Polymer liquids have the ability to contour surfaces, fill holes and cavities and also, through capillary pressure, they may be forced into pores on the substrate, creating a mechanical keying. Efficiency of mechanical interlocking depends upon wetting, since unwetted areas give rise to stress concentration that initiates failure or delamination. From the standpoint of thermodynamics, the maximum reversible work of adhesion $W_a$ is given by Dupré's equation and the spreading coefficient, $S_{CN}$, is described by the Cooper-Nuttal relation:

$$W_a = \gamma_\alpha + \gamma_\beta - \gamma_{\alpha\beta} \qquad (1)$$

$$S_{CN} = \gamma_\alpha - \gamma_\beta - \gamma_{\alpha\beta} \qquad (2)$$

where $\gamma_\alpha$ and $\gamma_\beta$ are the surface tensions of materials $\alpha$ and $\beta$ respectively and $\gamma_{\alpha\beta}$ is the interfacial tension between $\alpha$ and $\beta$. Therefore $$W_a = S_{CN} 2\gamma_\beta,$$

indicating that strong wetting and high surface tension promote adhesion. On the other hand, it has been observed that interfacial tension, $\gamma_{\alpha\beta}$, was even more important in determining adhesive strength: the lower the $\gamma_{\alpha\beta}$, the higher the adhesive strength. In turn, $W_a$ and $\gamma_{\alpha\beta}$ relate to surface energy associated with the nature of atomic or molecular bonding. Depending upon the distance between discrete particles near the interface, the type of interaction is either mostly long-range or short-range. Lifshitz-van der Waals forces may be attractive or repulsive and are effective up to 1.0 nm. Strong Coulombic forces have a range near 0.3 nm, and involve chemical, covalent and ionic bonds. In the case where the separation between particles is less than 0.3 nm, molecular interaction across the interface, such as donor-acceptor or acid-base interaction, can make a major contribution to adhesive strength.

Structural morphology of intermixing of the materials is another governing factor in the determination of interfacial tension. Metals feature ordered crystalline lattices, while polymers have disordered, loosely entangled morphologies. For such a combination of materials with widely different structures, the building of bonding forces implies that complex mechanisms come into play. Polymer molecules must diffuse ($\tau_D \propto N^2$, for short chains) or reptate ($\tau_R \propto N^3$, for entangled chains) so that segments become anchored on the substrate. When the number of grafted chains per unit area, $\Sigma$, is small, the anchored molecules tend to coil up near the surface in the shape of isolated mushrooms or pancakes with average thicknesses $d_i \approx R_g \approx 1N^{\frac{1}{2}}$. As $\Sigma$ increases, the coils begin to overlap and interchain stresses associated with attractive osmotic forces and repulsive entropic forces cause the molecules to stretch out perpendicularly to the surface, like buoy lines. At equilibrium additional chains are repelled and the final structure is that of a brush with constant concentration profile. The present account is only schematic, yet it retains the basic ideas that constitute the state of the art. Although the theory is mostly supported by experiments with polymer solutions, it has been argued that melts behave similarly, and recent measurements of dynamic response with the SFA appear to confirm this.

The solidification phenomenon is not clearly understood and moreover so at interfaces. For block polymers, one observes effects of surface-induced orientation associated with surface free energy differences between molecular constituents. In the case of homopolymers, other more indirect measurements suggest that the hydrodynamic layer in the melt is frozen in. In the present case where the PP polymer has the ability to produce crystals, surface energy effects may influence growth behavior. For example surface roughness may be a site for heterogeneous nucleation, resulting in highly anisotropic domains, the so-called transcrystalline region.

The overall picture that emerges can be summarized by turning to FIG. 1. After being attached to the substrate (thickness $d_s$) some of the polymer chains may stretch out perpendicularly to the surface, forming molecular bridges between the adherend and the bulk of the adhesive (thickness $d_p$). There results a thin interface layer, $d_i \approx R_g$, of a material with properties different than those of the bulk polymer. This interfacial bonding layer serves to transfer mechanical load between the adherend to which molecules are solidly attached and the adhesive per se, where the molecules arrange into a disordered lattice. It is precisely this layer of material which is probed with the method of this invention. It is assumed that each component in the multilayer sample is made up of an isotropic and homogeneous material that is rigidly bonded (non-slip boundary condition) to neighboring layers at interface planes, and furthermore that the interfaces themselves are continuous and homogeneous.

Ultrasonic techniques involve the use of low amplitude ( stresses $\sigma \approx 10^2$ Pa and strains $\epsilon \approx 10^{-8}$) high frequency ($f$, in the MHz range ) mechanical waves to measure the elastic and viscous properties of materials. Preferably, the signal should be a pulsed signal, each pulse being of a duration in time of approximately equal to or less than 100 ns. Preferably, the pulse spectrum amplitude is approximately Gaussian in shape, the center frequency of the pulse being between 10 and 50 megahertz. It is possible to perform the method of this invention with a single pulse, however it is preferable to use a train of pulses, wherein the time interval between pulses is greater than 0.1 millisecond.

For isotropic elastic materials it may be shown that the displacement vector $\zeta$ is given by:

$$\rho \frac{\partial^2 \xi}{\partial t^2} = (K + 4\mu/3)\nabla\nabla \cdot \xi - \mu \nabla \times \nabla \times \xi \quad (3)$$

where $\rho$ is the density, and two independent coefficients, namely the bulk modulus, K, and the shear modulus, $\mu$, completely describe elastic behavior. In turn, one is led to introduce the dilatational or longitudinal modulus, $$L = K + 4/3\mu.$$

Specializing to plane waves in unbounded media, when the source of ultrasound oscillates harmonically with angular frequency $\omega = 2\pi f$, and the movements are polarized along the z axis, the solution is of the form:

$$\Phi = A \exp i(\omega t - k_p z) + B \exp i(\omega t + k_p z) = \Phi^+ + \Phi^- \quad (4a)$$

whereas for polarization normal to the z axis the solution is:

$$\Psi = C \exp i(\omega t - k_s z) + D \exp i(\omega t + k_s z) = \Psi^+ + \Psi^- \quad (4b)$$

where A, B, C, D, are arbitrary constants depending on boundary conditions. The quantities $\Phi$, and $\Psi$, designate any of the field variables (strain, stress, particle displacement, velocity and acceleration, temperature, and entropy) that undergo sinusoidal change due to the ultrasonic source. The + and − signs refer to waves propagating forward in the +z direction away from the origin and backward in the −z direction toward the source. The wave numbers $k_p$ and $k_s$ for longitudinal (P-waves) and shear waves (S-waves) are related to the wavelengths, $\Lambda_p = 2\pi/k_p$ and $\Lambda_s = 2\pi/k_s$, and to frequency through the dispersion relations, $k_p = \omega/c_p$ and $k_s = \omega/c_s$, where $$c_P = \sqrt{L/\rho} = \sqrt{\left(K + \frac{4}{3}\mu\right)/\rho} \qquad c_S = \sqrt{\mu/\rho} \quad (5)$$

are the different phase velocities of sound.

When an elastic wave of either type reaches a rigid, slip-free interface between different media, 1 and 2, certain boundary conditions must be satisfied that insure continuity for 1) the normal displacement, 2) the tangential displacement, 3) the normal stress, and 4) the tangential stress. For longitudinal P-waves at normal incidence ($\theta_0=0$), at the boundary between two semi-infinite media, one derives simple expressions for the reflection ($r_p$) and transmission ($t_p$) coefficients defined as the ratio of the stress amplitude, respectively, in the reflected, $\sigma_1^-$, and transmitted, $\sigma_2^+$, waves, to that in the incident wave $\sigma_1^+$:

$$r_P = \frac{\sigma_1^-}{\sigma_1^+} = \frac{Z_2 - Z_1}{Z_2 + Z_1}, \, t_P = \frac{\sigma_2^+}{\sigma_1^+} = \frac{2Z_2}{Z_2 + Z_1} \quad (6)$$

where $Z_1 = \rho_1 c_{P,1}$, and $Z_2 = \rho_2 c_{P,2}$ is the acoustic impedance for medium 1 and 2 respectively. One may also write similar relationships for shear waves. In reference to electrical impedance, the acoustic impedance is the ratio of the acoustic stress, $\sigma$ (analog to voltage) to the displacement velocity, $\partial \xi / \partial t$ (analog to current density). In the case where the media have finite dimensions, standing waves may form so that the expressions for Z, $r_p$ and $t_p$ are not so straightforward. In the two dimensional problem where the wave is oblique ($\theta \neq 0$, FIG. 1) with respect to the normal (z axis) to the surface (x-y plane), the boundary conditions give rise to mode conversion whereby there are two components for the reflection, a P-wave and an S-wave, and likewise for the refraction. This may be expressed in terms of the analog of Snell's law in the case of light:

$$\frac{\sin\theta}{c} = \text{constant} \quad (7)$$

where $\theta$ is the angle with the normal to the surface for any wave component and c is the sound velocity for that component. Therefore, there are five contributions to each displacement, and although the problem is tractable, the final equations are very complicated.

Part of mechanical energy is extracted from the wave which gives rise to damping or attenuation. Using $\Gamma$ for the generalized instantaneous amplitude with maximum value $\Gamma_o$ and a for the attenuation, both P-waves and S-waves may be represented by:

$$\Gamma = \Gamma_0^{\mp} \exp(-az) \, Re\{\exp i\,[\omega t \pm k'z]\} \quad (8)$$

The presence of attenuation implies that the generalized wavenumber is complex, $k^* = k' + ik'' = (\omega/c)(1 - iac/\omega)$, and thereby also the acoustic impedance, $Z^* = \rho\omega/k^*$. With this definition for a, the fractional energy loss per cycle per unit volume is equal to $2a\Lambda$. Provided $ac/\omega \ll 1$, as is often the case, a and c are related to the real and imaginary parts of the generalized complex modulus, $M^* = M' + iM''$, through:

$$M' = \rho c^2, \, M'' = 2\rho a c^3/\omega \quad (9)$$

and the logarithmic decrement, $\tan\delta = 2ac/\omega = M''/M'$, expresses the phase lag for the response to a perturbation.

For homogeneous polycrystalline metallic materials thermal gradients are set up over distances corresponding to the size of the crystallites, resulting in damping by thermoconduction, $a_{th} \propto f$. Also, grain boundaries are sites for the scattering of sound, which is another cause for attenuation, $a_{sc} \propto f^4$. In common metals, the attenuation is a combination of losses by thermoconduction and scattering and is usually expressed through a phenomenological equation:

$$a_{met} = c_1 f + c_2 f^2 + \ldots \quad (10)$$

where $c_1, c_2, \ldots$ are constants that are determined experimentally.

The propagation of ultrasound in polymers is of great interest and has been the object of active investigation by the applicants. Ultrasonic strain modifies thermal equilibrium in the polymer, and internal processes occur on a time scale f during which the system relaxes towards equilibrium. Such a mechanism being irreversible is accompanied by an increase of internal entropy and energy dissipation. Because of the small strains, the ultrasonic wave essentially probes small movements associated with the mobility of segmental units in the polymer chains. Therefore $\tau$ is related to a Rouse type relaxation time, quite different from that for large strains in usual rheology experiments, and which is closer to $\tau_D$, or $\tau_R$. For a sinusoidal excitation, conditions of linearity insure that the response is also sinusoidal; then the steady state solution for the complex dynamic modulus, $M^*(\omega) = M'(\omega) + iM''(\omega)$, is:

$$\frac{M'(\omega) - M_0}{M_\infty - M_0} = \frac{(\omega\tau)^2}{1 + (\omega\tau)^2} \quad (11)$$

$$\frac{M''(\omega)}{M_\infty - M_0} = \frac{\omega\tau}{1 + (\omega\tau)^2}$$

where $M_0$ is the so-called relaxed modulus in the zero frequency limit and $M_\infty$ the unrelaxed modulus corresponding to infinite frequency. Actually this description implies only one degree of freedom and is not complete for polymers. However, the operational assumption is made, of a single effective relaxation time $\tau$.

The multilayer structure shown in FIG. 1 can be viewed as a complex acoustic transmission line. In traveling from medium i to medium i+1, the change of acoustic impedance, from $Z_i^*$ to $Z_{i+1}^*$, causes the wave to be partly reflected and partly transmitted at the interface which results in standing waves with intricate patterns of constructive and destructive interference. Albeit usual transmission line theory is valid, actual application is quite involved due to: 1) finite thickness of the layers, 2) numerous interface planes, 6 in the case at hand, 3) different laws for the elastic metal and viscoelastic polymer, 4) mode conversion for 2-D propagation, 5) finite width of the acoustic beam and nonplanar wave fronts. Also, polymer viscoelasticity is a form of negative feedback mechanism that relates to nonlinear behavior with respect to frequency and thus may lead to peculiarities in the response function.

In this case one must return to Equations (4) that are coupled through the boundary conditions and resolve the system for the unknown coefficients in each layer. The solution involves a great deal of analytical work but the final operational result can only be obtained numerically. In the applicant's publication referred to above, a recurrence relation is described for transferring stresses and displacements from one interface to another using a so-called Transfer Matrix Approach. Also described is a numerical scheme for calculating the reflection and transmission coefficients, that is very efficient and yet robust, so as to overcome problems associated with computational stability.

Test Results

Figure 2A:
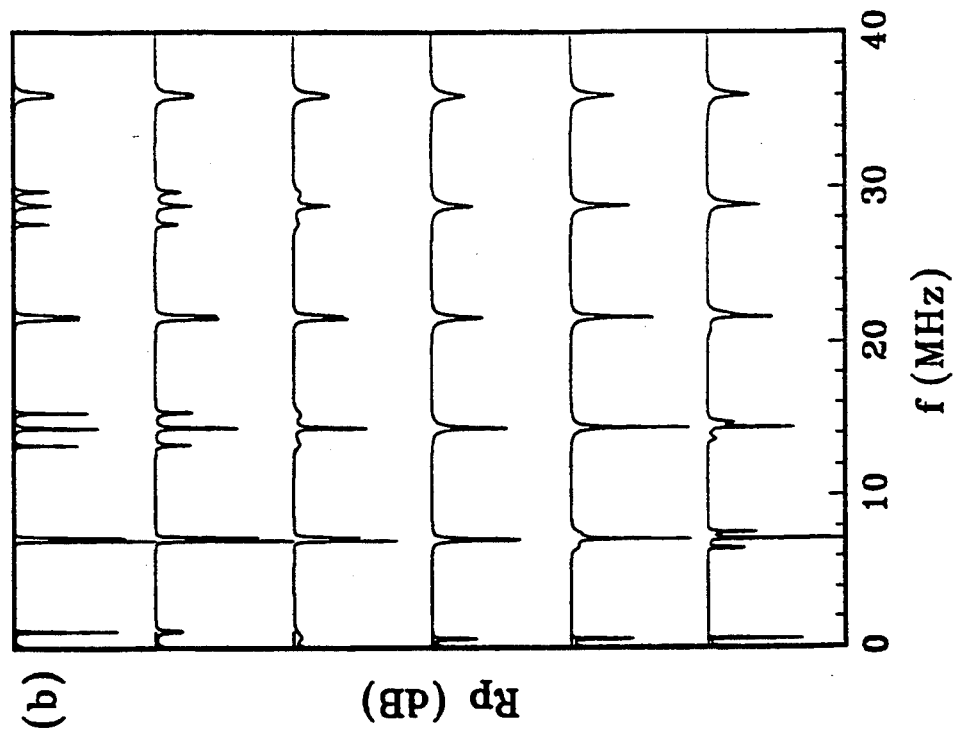
FIG. 2a is a numerical simulation graph of amplitude versus frequency (dB) for steel-polymer-steel assuming rigid conditions $\tau = 500$ ns and starting from the bottom, $d_p = 0, 10, 30, 80, 100, 120$ μm.

As a means of illustration, a numerical experiment was performed on a steel ($d_s = 400 \, \mu m$) / polypropylene ($d_p$)/steel ($d_s$=400 mm) multilayer under water immersion and the frequency dependence for the amplitude of the reflection coefficient $R_p=|r_p|$ in the case of P-waves at normal incidence was computed. The acoustic properties for water, stainless-steel, and bulk PP are given in Table 1 and will be explained later. First, the assumption of rigid boundary conditions with no interfacial bonding layer, $d_i=0$ is made. FIG. 2a illustrates the behavior for $R_p$ (24 dB between tick marks) in the frequency range $f=0$ to 40 MHz; for the relaxation time associated with P-waves $\tau_{p,P}=500$ ns is used, and going from bottom to top, the different traces correspond to polymer thicknesses $d_p=0$, 10, 30, 80, 100, and 120 μm respectively. The results show up in series of dips for $R_p$ that may be understood in terms of coupled harmonic oscillators, as suggested by the occurrence of standing waves in each layer. The characteristic frequency for an isolated oscillator vibrating in the half-wavelength mode is $f=nc/(2d)$, n=1, 2 ... The lower trace, for $d_p=0$, when the two steel plates are welded to one another, corresponds to a single oscillator with $d=2d_s=800$ μm, so that resonant features appear regularly at frequencies $f_{2s}=n$ 3.60 MHz. In the next trace, the polymer film acts to couple the steel plate vibrators. On one hand, the layered structure constitutes a lumped oscillator having its own eigenfrequency, which is the origin for the dip near 1 MHz. On the other hand, the coupled oscillators represent a physical system with normal modes given by:

$$f=f^+ \pm[\chi^2+(f^-)^2]^{\frac{1}{2}},$$

where $f^+(f_1 f_2)/2$ and $f^-=(f_1-f_2)/2$, $f_1$ and $f_2$ being the natural frequencies for the freely oscillating vibrators and $\chi$ a coupling constant. Here, since the oscillators are perfectly tuned, $f_1=f_2=f_s=n$ 7.20 MHz; therefore $f^-=0$ and $f=f^+ \pm \chi = f_s \pm \chi$. Assuming the polymer plays the role for the coupling $\chi$, there results the double dip features that tend to disappear as the oscillators become independent, near $d_p=30$ μm. However, this argumentation is only approximate due to standing waves in the polymer itself, as evidenced by the presence of triplets at higher values of $d_p$. In turn this suggests that each steel plate is itself coupled to the polymer, via an additional coupling constant.

Figure 2B:
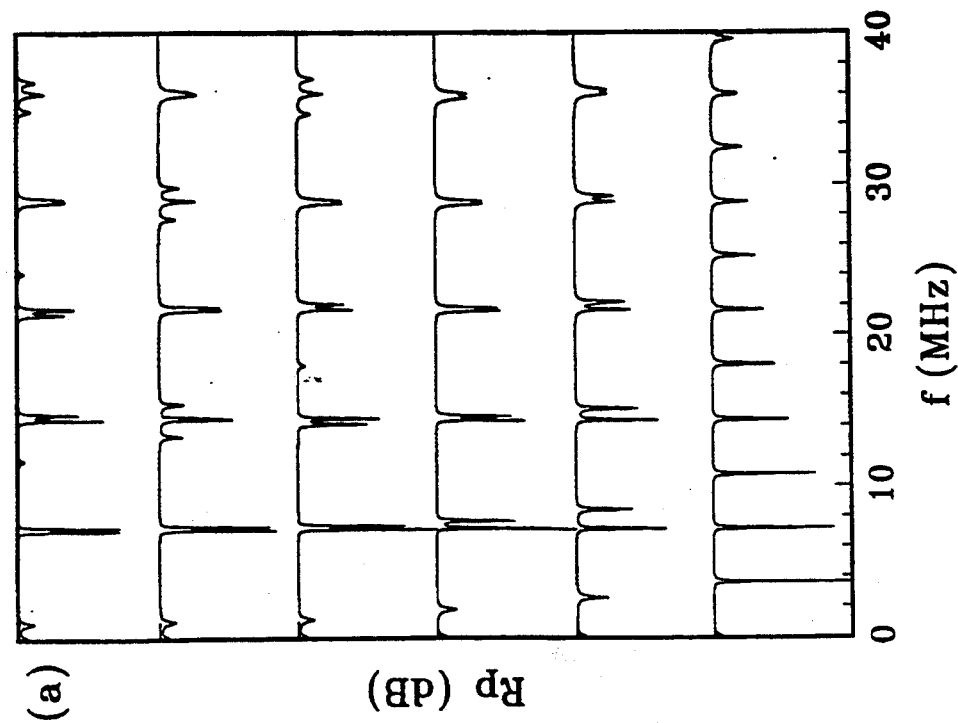
FIG. 2b is a numerical simulation graph of amplitude versus frequency (dB) for steel-polymer-steel assuming rigid conditions, as shown in FIG. 2a, with $d_p = 100$ μm and starting from the bottom, $\tau = 0.1, 1.0, 10, 10^2, 10^3, 10^4$ ns.

Still under the assumption of rigid boundary conditions with no interface layer in the steel ($d_s=400$ μm)/polypropylene($d_p$)/steel ($d_s=400$ mm) multilayer, in FIG. 2b thickness for the polymer, $d_p=100$ μm is set, and the influence of the relaxation time of the polymer is investigated: starting from the bottom $\tau_{p,P}=0.1$, 1.0, 10, 100, $10^3$, and $10^4$ ns. As in FIG. 2a, one observes a low frequency feature, between 0.5 and 2.0 MHz corresponding to an eigenmode for the lumped oscillator, and sharp minima at equally spaced frequencies, $f_{n+1}-f_n=7.2$ MHz, coinciding with resonant conditions in the steel plates. In the lower trace, $\tau_{p,P}=0.1$ ns, the resonance at 7.2 MHz corresponds to the limit $\omega\tau_{p,P}<<1$, where the polymer is liquid-like and the attenuation is small. These conditions promote mode coupling between the different layers, as manifested by triple-dip feature near 7.2 MHz. For larger values of $\omega\tau_{p,P}$ the attenuation increases rapidly and the satellite dips become smaller, leaving only the central feature for the resonance of the steel plate. For $\tau_{p,P}=10$ ns and frequencies above 7.2 MHz, the condition $\omega\tau_{p,P}>1$ prevails and the attenuation is large so the pattern approaches that of a single steel layer immersed in water, except for the low frequency feature where $\omega\tau_{p,P}<<1$.

For $\tau_{p,P}=10^3$ and $10^4$ ns, $\omega\tau_{p,P}<<1$, the attenuation is small and the polymer behaves solid-like. Then, because of the stiffer coupling, the resonance dips become narrower and the splitting becomes more pronounced.

In the example, the doublet/triplet features for resonance splitting constitute the most obvious indication of coupling between layers. Hence, for purposes of nondestructive evaluation, this method may be useful for probing the thickness of the polymer adhesive or the advancement of curing of adhesive joints. However such a test is only approximate since the results in FIG. 2 presuppose rigid bonding with no interface layer and do not make allowance for interfacial adhesion.

Interface Bonding Layer and Specific Stiffness (S)

The influence of an additional layer between the adherend and the adhesive in the sample was investigated: steel ($d_s=400$ μm)/interfacial bond layer ($d_i$)/polypropylene ($d_p=80$ μm)/interfacial bond layer ($d_i$)/steel ($d_s=400$ mm). Since the actual thickness ($d_i$ and moduli ($K_i^*$, $L_i^*$ and $\mu_i^*$) are unknown, relative quantities are considered, $d_i/d_p$, $K_i^*$, $L_i^*/L_p^*$, $\mu_i^*/\mu_i^*$. Equal relaxation times in the intermediate layer and the bulk polymer for P-waves, $\tau_{i,P}=\tau_{p,P}=\tau$, and S-waves, $\tau_{i,S}=\tau_{p,S}=\tau$ are initially assumed. The low frequency feature near 1.0 MHz which is the response for the composite vibrator when $d_p=80$ μm and $\tau=500$ ns (see FIG. 2a) was investigated. In FIG. 3a, the frequency $f_{max}$ was computed for the position of the resonance feature with respect to $L_i^*/L_p^*$ in the range from $10^{-5}$ to $10^3$, and starting from the left the different curves correspond to $d_i/d_p=10^{-5}$, $10^{-4}$, $10^{-3}$, $10^{-2}$ and $10^{-1}$ respectively. The results immediately suggest scaling behavior with respect to $d_i/d_p$. Following along those lines, in FIG. 3b, $f_{max}$ as function of $\overline{S}_p=(d_p/L_p^*)(L_i^*/d_i)$ was plotted, which indeed yields what may be considered as a universal master curve. A great number of simulations for other features at different frequencies were performed and also for the amplitudes of R and T which lead to the same conclusion: whenever $d_i$ is smaller than the acoustic wavelength $\Lambda$, the thickness and modulus are not independent parameters. Similarly, the propagation of S-waves could be described in terms of the reduced quantity $\overline{S}_s=(d_p/\mu_p^*)(\mu_i^*/d_i)$. In fact, the results are in line with a more analytical approach when the intermediate layer is considered as a small perturbation and when inertia terms are neglected. We mention that provided $\tau_{i,P}=\tau_{p,P}$, and $\tau_{i,S}=\tau_{p,S}$, $\overline{S}_p$ and $\overline{S}_s$ are real quantities. While $(d_p/L_p^*)$ and $(d_p/\mu_p^*)$ are ad hoc scaling constants, the parameters, $S_p=(L_i^*/d_i)$ and $S_s=(\mu_i^*/d_i)$ are the normal and transverse specific stiffness coefficients for longitudinal and shear waves respectively, and constitute the relevant variables for the problem. This is tantamount to the more intuitive idea of an effective viscoelastic spring $S=\Sigma k^*$, where, in a parallel arrangement, $\Sigma$ is the number of springs per unit area and $k^*$ the complex spring constant. In FIG. 3b, one observes saturation when $\overline{S}>100$, which points out the limiting sensitivity of the method for strong interfacial adhesion, corresponding to almost rigid boundary conditions (see FIG. 2).

Figure 4:
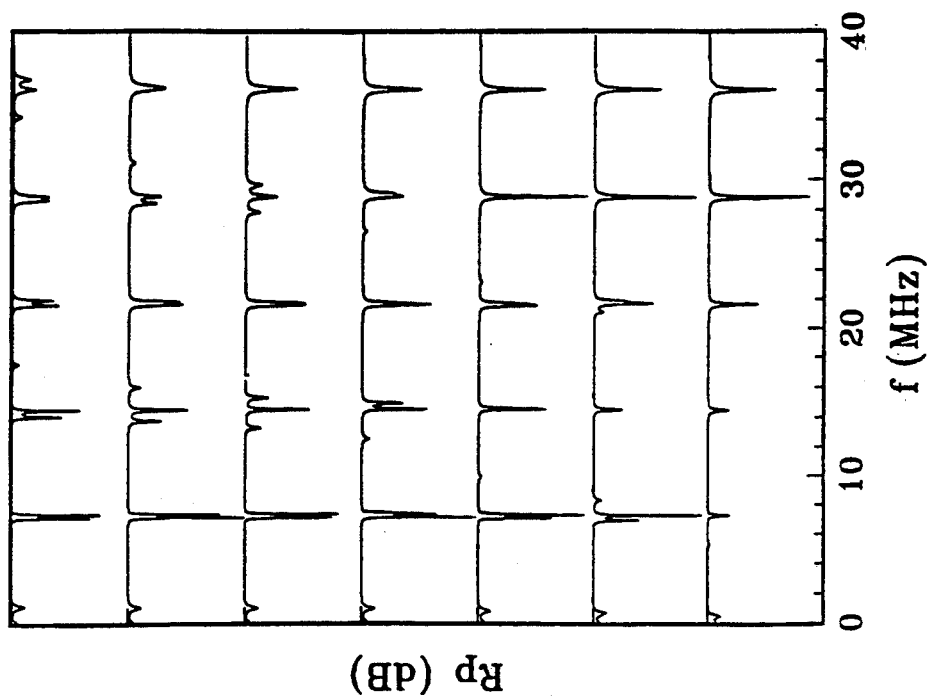
FIG. 4 is a numerical simulation graph of amplitude (dB) for $R_p$ versus frequency from bottom trace $\overline{S}_p = 0.48, 1.2, 2.0, 4.8, 7.2, 12.0,$ and 80.

In FIG. 4 the behavior of $R_p$ (24 dB between tick marks) for different values of $\overline{S}_p$ (bearing in mind the present value $d_p=80$ μm) is shown: starting from the bottom $\overline{S}_p=0.4$, 1.2, 2.4, 4.8, 8.0, 12.0, and 80. The smallest value, $\overline{S}_p=0.4$, represents a very weak interface, and indeed it was verified that the pattern is similar to that for a single steel plate with air backing. For $\overline{S}_p=1.2$, there appears a small double dip feature near 8 MHz, that shifts to higher frequency for larger values of $\overline{S}_p$, and eventually contributes to the resonance at 14.4 MHz. Although this pattern seems to repeat itself with increasing frequency, no evidence was found of a true periodicity. Finally, when $\overline{S}_p>80$, the behavior approaches that in FIG. 2a, corresponding to rigid bonding.

Overall, comparing FIGS. 2a and 4, it is obvious that the intermediate bonding layer affects the ultrasonic spectrum, depending on specific stiffness. Given the great number of paths and collisions for the wave, the final result for the output signal is difficult to predict and highly dependent on details for the geometry (thickness) and physical properties (density, velocity and attenuation of sound), of the individual constituents. It is precisely this complexity that causes the "interferometric device" to be so sensitive to minute changes in interfacial properties. In some sense, because of the large contrast of acoustic impedance, the metal layers in the metal/polymer/metal assembly play the same role as the mirrors in a Fabry-Pérot interferometer.

The approach in accordance with the invention is a novel approach; it includes and probes interfacial properties at the microscopic scale and leads to quantitative characterization of interfacial forces in terms of specific stiffness, $S_p$ and $S_s$.

Experimental Materials

The samples chosen for demonstrating the method are the same as those used in the simulations, namely: steel ($d_s=400$ μm)/polypropylene ($d_p$)/steel ($d_s=400$ mm), where interfacial adhesion was modified through chemical action on both the PP polymer, and the metal surfaces. Polypropylene is a non-polar and chemically non-reactive material that exhibits low wettability and very weak adhesion to metals. The PP polymer was made adherent to stainless steel by radical grafting of glycidyl methacrylate (MAG, 142 g/mol) containing ester and epoxide functional groups. The virgin PP material, designated 61400AP, was provided by the Appryl Company, France in powder form with average grain size near 250 μm. Using gel permeation chromatography (GPC) the number average molecular weight, $\overline{M}_n=48\,000$ g/mol, and the weight average molecular weight, $\overline{M}_w=205\,000$ g/mol. In order to limit thermal degradation, all chemical actions on the material were performed in the solid state and modifications were mainly localized in a 30 μm shell around the grains. Peroxide structures were generated by flowing a $O_2$—$O_3$ mixture on the PP powder contained in a fluidized bed reactor. Rheology measurements established that approximately 0.8 grafting sites per chain were created. The peroxidized powder was mixed with liquid glycidyl methacrylate and the temperature was brought to 115° C. where the peroxides decomposed, initiating grafting and polymerization of the MAG comonomers. The reaction was carried out for 3 hours. Using Fast Fourier Infrared (FTIK) spectroscopy it was found that the polymer contained 6.5% weight of MAG. This corresponds to circa 20 MAG comonomers for each PP chain, meaning that the PP-MAG polymer also contained short MAG macromolecules.

Starting with austenitic stainless steel (Z6NT 18-09) sheet with thickness $d_s=400$ μm, two different substrate materials were prepared. In one case, the metal was thoroughly cleansed and etched in an acid solution (5% HF+15% $HNO_3$) while in the other case, the cleansed and etched metal was also anodized in a sulfochromic solution. Whilst the overall rugosity for the substrates was $\approx 200$ nm, observations revealed mesopores with diameters between 4 and 10 nm on anodized surfaces. On the other hand, XPS showed that anodized surfaces were enriched with Cr and O elements and also that the concentration of hydroxidized species (M—OH and MO—OH) exceeded that of oxidized species (M—O).

Uniform films of grafted polypropylene (PP-MAG) were prepared by molding the powder at constant pressure, p=1.0 MPa, and temperature, T=200° C., for 5 or 6 minutes. The substrate-film-substrate sandwich was left for 6 minutes between the platens of a press where p=1.0 MPa and T=200° C. From measurements of total multilayer thickness, it was deduced that $d_p=80\pm1.0$ μm for the thickness of the adhesive. Destructive shear tests (ASTM D 1002-72) demonstrated definite enhancement of practical adhesion due to anodization: for samples prepared with cleansed substrates, (cl), interfacial failure occurred at $\sigma_c(cl)=6.1\pm0.4$ MPa while for samples with anodized substrates, (an), cohesive failure happened near $\sigma_c(an)=12.6\pm1.1$ MPa. Application of SEM, XPS and IR-micro-spectrometry techniques following failure showed residual polypropylene films on the anodized substrates, with thicknesses near 10 nm and evidence for C—O—C and C—O—H groups associated with MAC entities grafted to the surfaces. Therefore, for the samples, stronger adhesion is obtained when molecules with ester and epoxide groups are made to interact with polar groups on the anodized substrates.

Ultrasonic Technique

Figure 5:
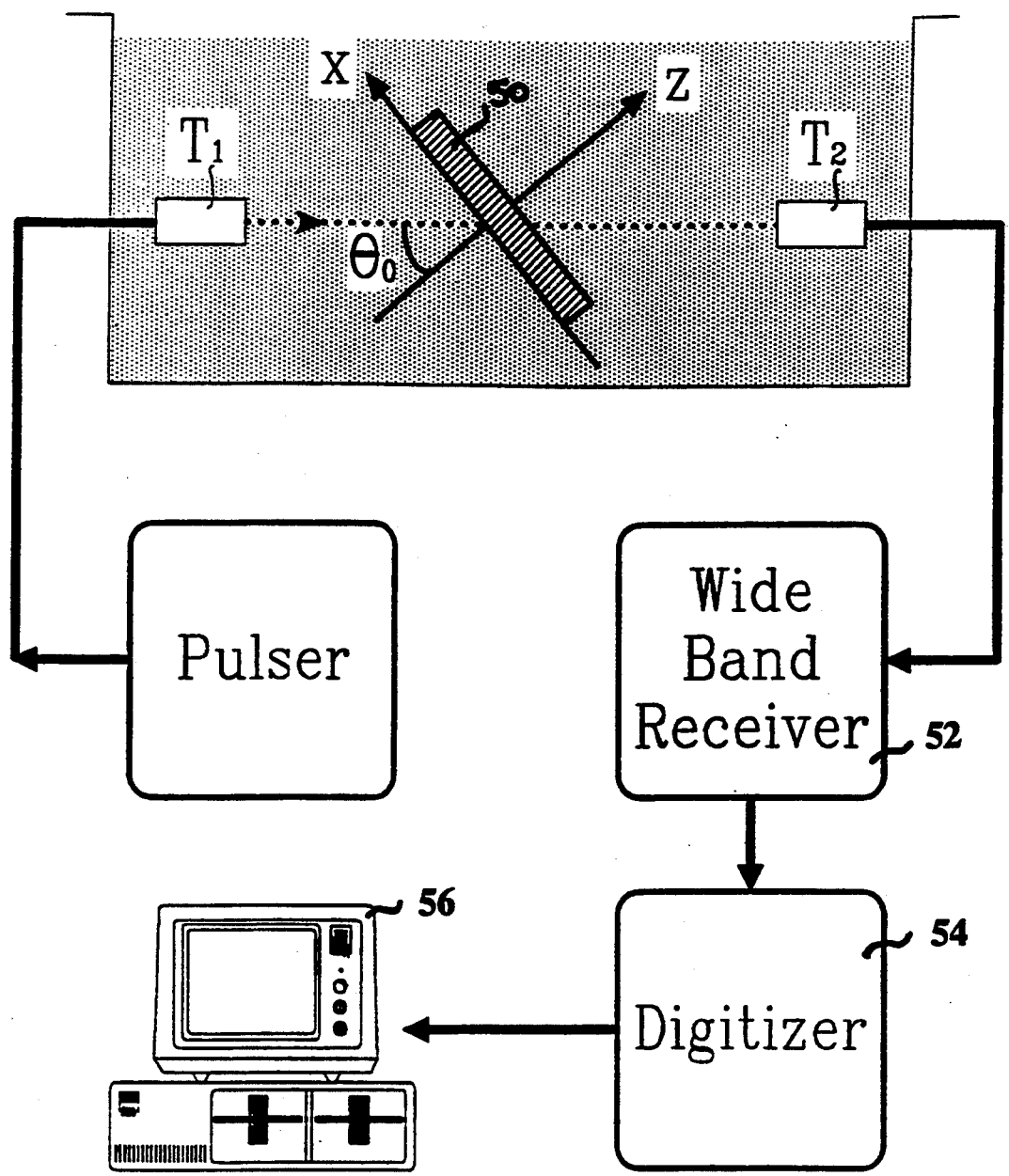
FIG. 5 is a schematic diagram of an ultrasonic setup showing a sample to be tested immersed in water.

In an experimental setup shown in FIG. 5, a sample 50 was placed between a pair of coaxially aligned transducers T1 and T2, and the assembly was immersed in water that acted to couple the sound wave in the material. The setup was maintained at a constant temperature T=23°±0.5° C. and care was taken to prevent infiltration of water and humidity into the multilayer sample. The sample 50 could be rotated around a y axis which, in accordance to Snell's law, allowed launching longitudinal and shear waves in the sample. Various broadband transducers T1 and T2 with center frequencies from 20 to 50 MHz were used. The distance between sample 50 and transducers T1 and T2 was chosen so as to minimize spurious effects due to beam diffraction. It was established that the acoustic beams were Gaussian, with half-widths near 2.0 mm at the arrival site on the sample. Operation could be performed either in the reflection mode with one transducer acting both to emit and receive the ultrasound or in the transmission mode with two transducers, one for the emission the other for the reception. The emitting transducer was energized with a generator (Metrotec MR-203 not shown) that produced short 50 to 200 ns high voltage 200 V pulses with a repetition rate around 1.0 kHz. The signal from the receiving transducer was fed to a Tektronix 7854 digitizing oscilloscope 54 via a broadband 100 MHz receiver-amplifier 52 (Metrotec MR-106). The digitizer 54 was linked to a computer 56 where the signals could be Fourier-transformed to the frequency domain and deconvolved with a reference spectrum in order to obtain the spectra associated with the reflection and transmission coefficients.

Figure 6B:
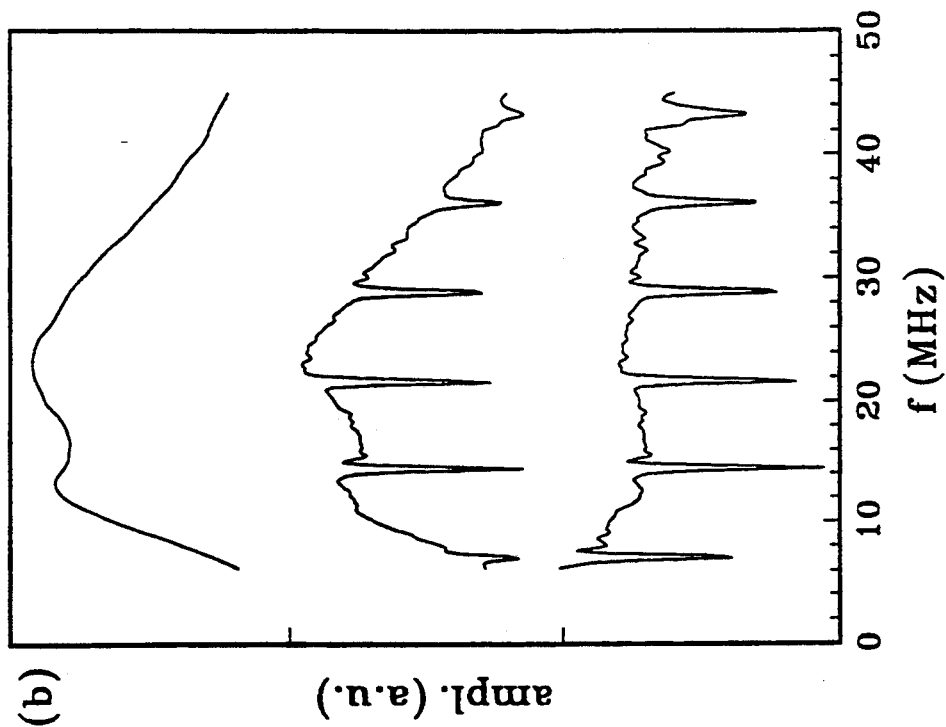
FIG. 6b is a graph in the frequency domain relating to the time domain traces of FIG. 6a, the lower trace in FIG. 6b, being a deconvolved normalized trace derived from the upper two traces.
Figure 6A:
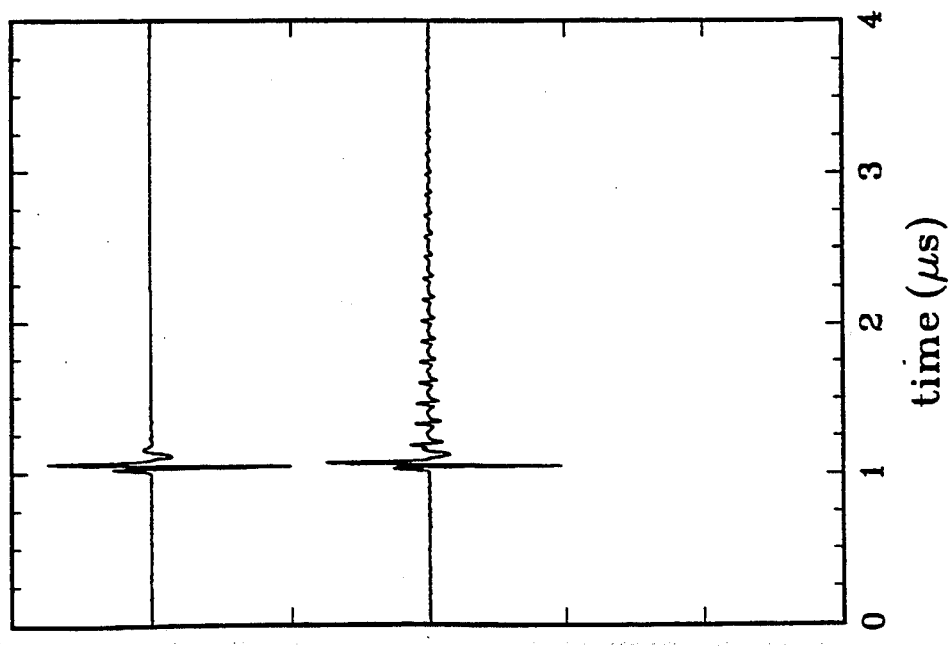
FIG. 6a is a graph of amplitude versus time of two ultrasound traces.

Referring to FIGS. 6a, the measurement of the acoustical properties of steel substrates is shown. The upper trace in FIG. 6a is the signal for specular reflection off a very thick piece of stainless steel that served as the reference for experiments in the reflection mode. The lower trace is the signal for reflection off a 400 μm thick substrate. A strong component due to specular reflection and small echoes with exponential decay corresponding to reverberations within the sample is shown. In principle, the time delay, Δt, between successive echoes, n and n+1, provides a measurement of the velocity of sound, $c_{P,s}=2d_s/\Delta t$, and accounting for reflection, $R_{sw}$, due to the acoustic mismatch between water and steel, the ratio for the amplitudes leads to the attenuation, $a_{P,s}=-(\frac{1}{2}d_s)\ln[(1/R_{sw}^2)(\Gamma_{n+1}/\Gamma_n)]$. However, the short pulse is not monochromatic and due to its finite duration, δt, it has a finite bandwidth, $\delta f \approx 2(1/\delta t)$, which allows measuring the frequency dependence of the velocity and attenuation. In FIG. 6b, the upper trace (1) is the frequency spectrum for the signal due to specular reflection in FIG. 6a, and the middle trace (2) is the spectrum for the reflection from the substrate. The bottom trace (3) is the deconvolved signal obtained by dividing the results in trace (2) by those in trace (1), and that represents the frequency dependence of the reflection coefficient, $R_P$, for the steel plate, independent of the characteristics of the measuring system. Likewise, the transmission coefficient at normal incidence, $T_P$, and oblique incidence, $T_\theta$, is found by deconvolving the signal transmitted through the sample with the reference spectrum obtained when the sample is removed. By fitting a model to such results, the P-wave and S-wave ultrasonic properties of the materials were determined, see Table 1. In a different experiment the ultrasonic properties of the PP-MAG material with regards to viscoelasticity were also investigated. Measurements of density, sound velocity and attenuation were carried out at constant pressure, p=1.0 MPa in the temperature range from 0° to 220° C. A strong relaxation feature with a maximum near 60° C. corresponding to $\omega\tau=1$ was observed. Although there was evidence of a broad distribution of relaxation times from $\tau \approx 10^5$ ns to $\tau \approx 10^{-2}$ ns, near T=23° C. it was estimated that $\tau_{p,P} \approx \tau_{p,S} \approx 500$ ns. The results in the region around T=23° C. could be fitted to the relaxation functions in equation (11) with the values for the relaxed and unrelaxed moduli as in Table 1.

Experimental Results

Referring to FIG. 7, some results in the time domain (signal amplitude versus time) are shown for the through transmitted signals obtained at normal incidence with two different pairs of transducers: in the case of FIG. 7a the center frequency was 15 MHz and the bandwidth close to 8.0 MHz, while in FIG. 7b the center frequency was 30 MHz, and the bandwidth near 30 MHz. Starting from the top in FIGS. 7a and 7b, the different traces correspond to 1) the reference signal in the absence of sample, 2) the signal from a 400 μm steel substrate, 3) the response for a multilayer made with anodized substrates, and 4) the signature for a multilayer with cleansed only substrates. In the time domain, one can neither identify nor separate out echoes for the different constituents in the multilayer, due to the fact that the wavelength, $\Lambda_P \geq 200$ μm, is not small compared to the path length $d_s$ or $d_p \approx 200$ μm. On the other hand one observes that adhesion strength can have a marked influence on the signal, depending on transducer characteristics. Therefore, the measurements effectively embody information on adhesion; however, in the time domain the signals are too complex to be unscrambled and analyzed.

Figure 8A:
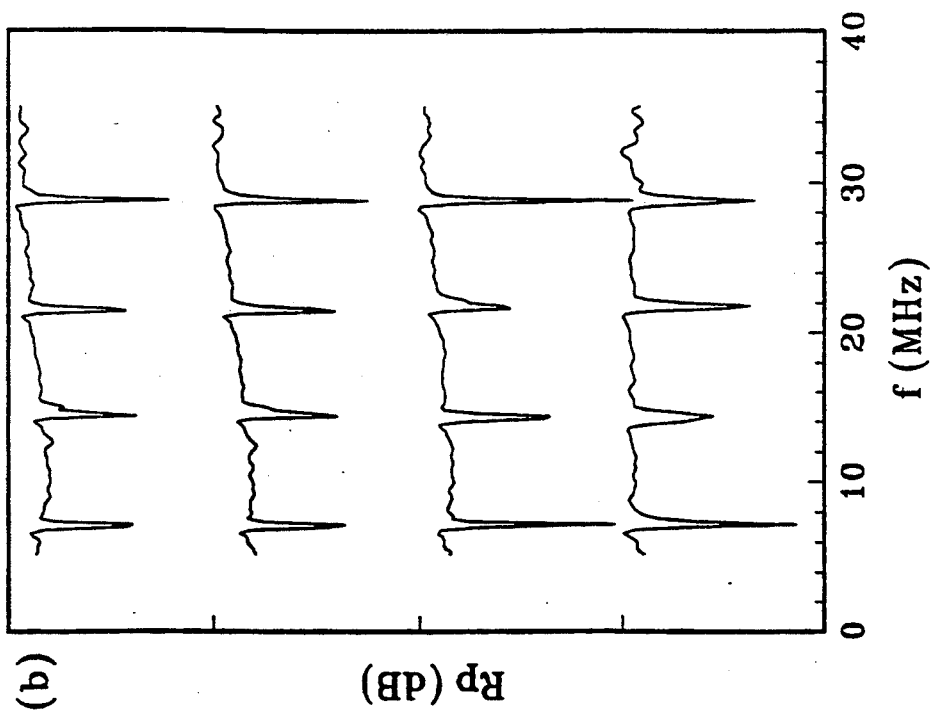
FIG. 8a is a graph of amplitude versus frequency of reflection coefficient, at different locations on a multilayer for anodized substrates and high adhesion.
Figure 8B:
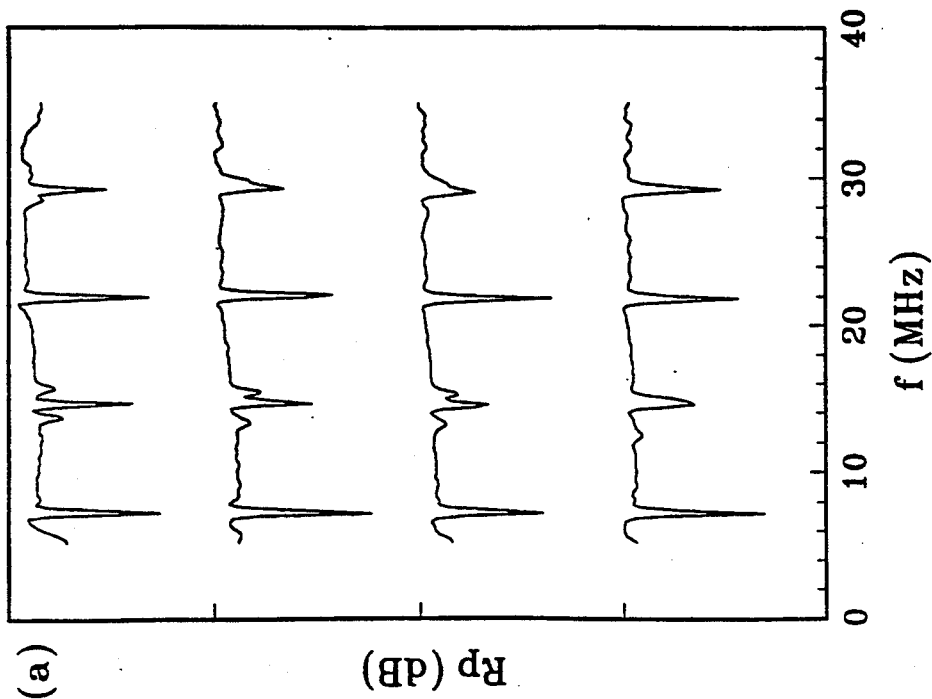
FIG. 8b is a graph of amplitude versus frequency of reflection coefficient, at different locations on a multilayer for cleansed only substrates and weak adhesion.
Figure 9A:
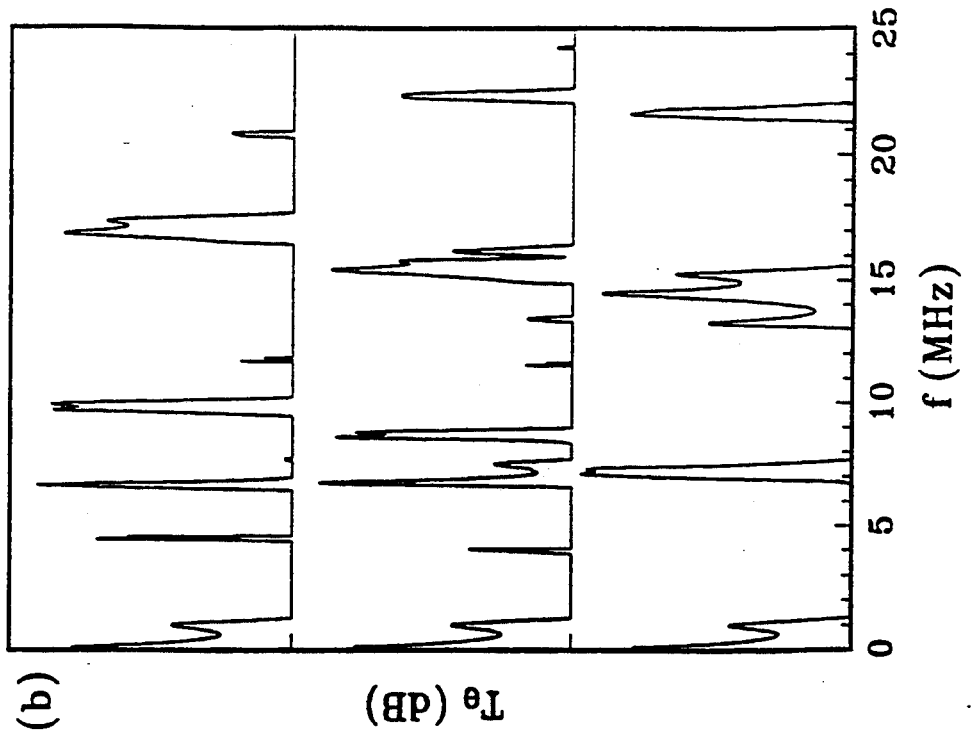
FIG. 9a is a graph of amplitude versus frequency of a transmission coefficient for a multilayer with anodized substrates and strong adhesion at different orientations from bottom to top, $\theta = 0, 5,$ and 8 degrees as taken by actual measurements.
Figure 9B:
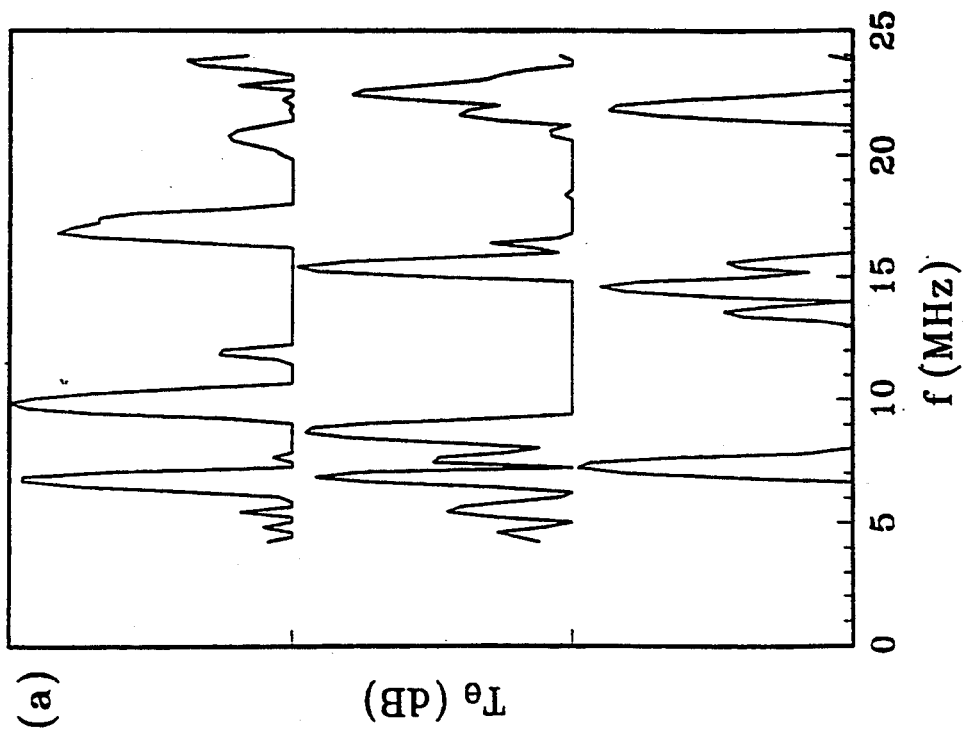
FIG. 9b is a graph of amplitude versus frequency of transmission coefficient for a multilayer with anodized substrates and strong adhesion at different orientations from bottom to top, $\theta = 0, 5,$ and 8 degrees as plotted from simulations with $\overline{S}_p = 7.2$.

Now turning to FIG. 8, the behavior for the frequency spectrum of the reflection coefficient at normal incidence is shown, $R_p$ (24 dB between tick marks) corresponding to different locations on the specimens with anodized substrates. From the data in FIG. 8a, the samples appear rather homogeneous and one clearly observes resonance splitting, indicative of strong coupling between the different layers. Going from the top down, traces 1), 2) and 3) are in order of decreasing coupling strength. Using the model, attempts were made to reproduce these patterns by investigating the influence of $\overline{S}_P$ and $\tau_{i,P}$. In FIG. 8b results of simulations are shown that matched best the traces in FIG. 8a: going from top to bottom, spectra 1), 2) and 3) where obtained with $\overline{S}_P=11.0$, 7.0 and 6.0 respectively, and $\tau_{i,P}=\tau_{p,P}=\tau$, that is with equal relaxation times in the bonding layer and the bulk polymer. FIG. 9a illustrates data for the samples with the cleansed only substrates. In this case, the material seems to be less homogenous and there is no evidence of frequency splitting, suggesting small coupling. Going downwards from the top, traces 1), 2) and 3) are in order of decreasing adhesion strength. FIG. 9b reproduces theoretical spectra that matched best the experimental curves in FIG. 9a: from top down, spectra 1), 2) and 3) correspond to $\overline{S}_P=2.8$, 2.0 and 0.8 respectively, and $\tau_{i,P}=\tau_{p,P}=\tau$. Compared to the samples with anodized substrates, the results for the samples with cleansed only substrates indicate lower adhesion forces, even though there were no signs of delaminations. For waves at normal incidence only $\overline{S}_P$ is relevant, but for oblique incidence, both $\overline{S}_P$ and $\overline{S}_s$ operate.

Figure 10B:
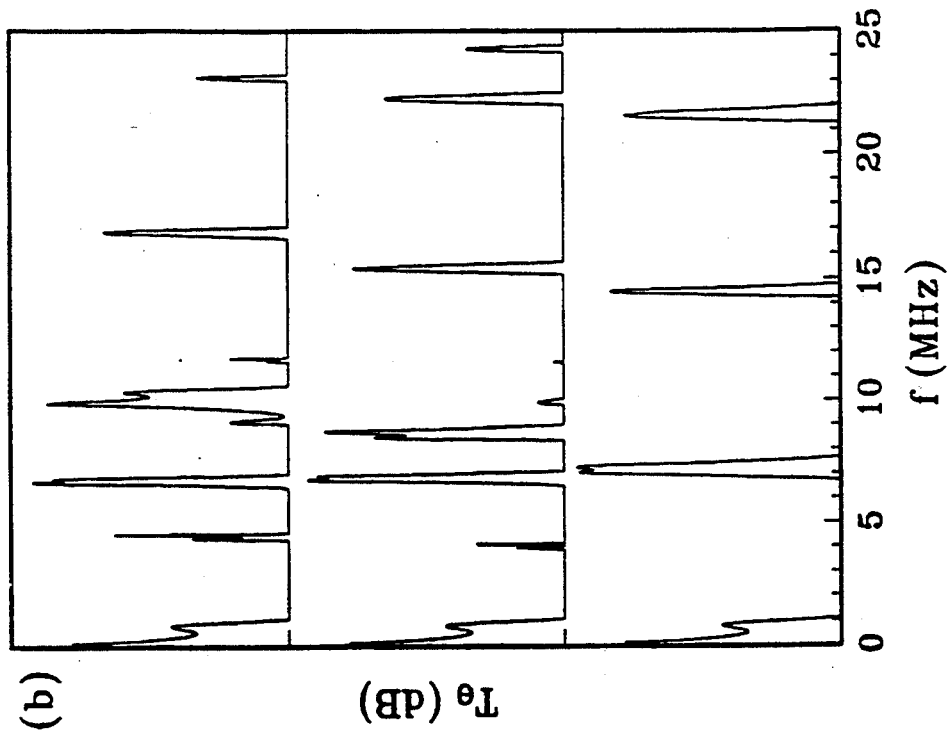
FIG. 10b is a graph of amplitude versus frequency of transmission coefficient for a multilayer with cleansed substrates and weak adhesion at different orientations from bottom to top, $\theta = 0, 5,$ and 8 degrees as plotted from simulations with $\overline{S}_p = 2.0$.
Figure 10A:
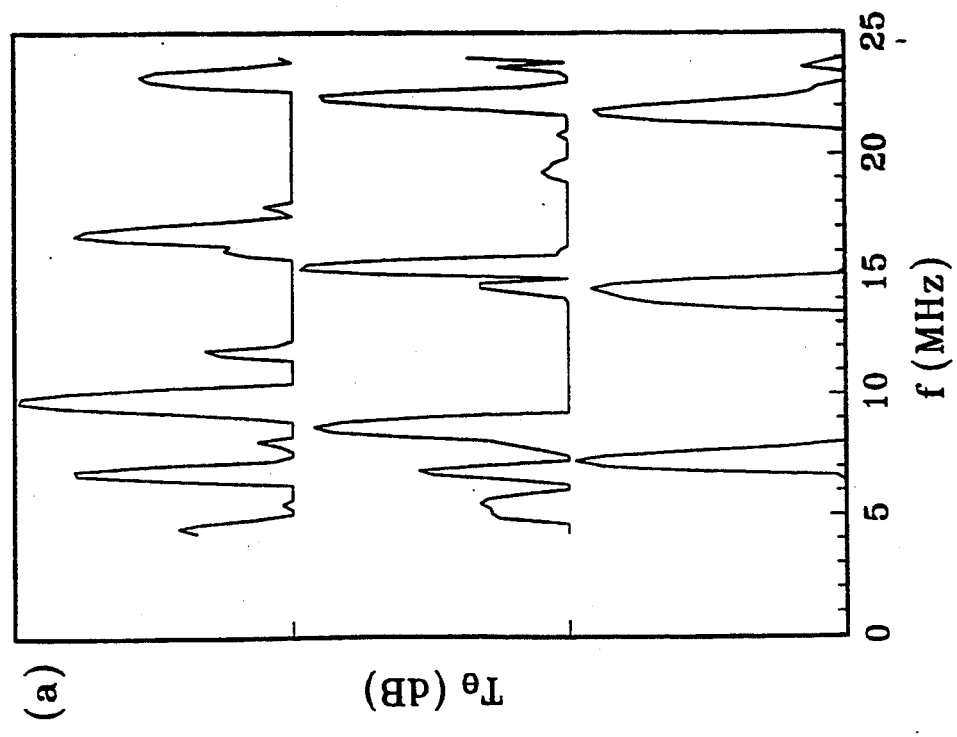
FIG. 10a is a graph of amplitude versus frequency of transmission coefficient for a multilayer with cleansed substrates and weak adhesion at different orientations from bottom to top, $\theta = 0, 5,$ and 8 degrees as taken by actual measurements.

In FIG. 10a results are shown for measurement of the transmission coefficient at oblique incidence $T_\theta$, in the case of a sample with anodized substrates. Going from the bottom up, the different traces 1), 2) and 3) for $T_\theta$ (20 dB between tick marks) were measured at $\theta_0=0.0°$, 5.0°, and 8.0°, respectively. In comparison with the behavior for $R_P$ the spectra for $T_\theta$ are more complex and cannot be described with simple arguments. Overall, for oblique incidence the ultrasonic path length is longer, therefore the resonance features for P-waves are displaced to lower frequencies. Also manifestations related to S-waves are expected; however, they occur close to P-wave resonances and therefore they cannot always be clearly identified. In FIG. 10b simulations for a best fit to the data yield $\overline{S}_P=\overline{S}_s=7.2$ for strong adhesion with $\tau_{i,P}=\tau$ and $\tau_{i,S}=\tau$. Bearing in mind that sensitivity for the measurement diminishes below $f \approx 5$ MHz, the similarity between the experimental results and the simulations from the model is striking. Starting from the top in FIG. 11a experimental spectra are shown for $T_\theta$ (20 dB between tick marks) measured at $\theta_O=0.0°$, 5.0°, and 8.0° in the case of a sample with cleansed only substrates. FIG. 11b illustrates the best fit to our model, with $\overline{S}_P=\overline{S}_s=2.0$ which corresponds with conclusions for $R_p$ in FIG. 9. Comparing FIG. 10 and FIG. 11 shows that frequency splitting due to strong coupling between the layers is indicated for the feature near 15 MHz, at least for small values of $\theta_0$. Also longitudinal waves may be more sensitive than shear waves for differentiating between strong and weak bonding, indicating that adhesion is not a shear related problem only.

On the basis of recent developments the assumption was made that the modulus, $M_i^*$, for the interface layer was described by a relaxation function as in equation (11). Using $\tau_i = \tau_p = \tau$ both the amplitude and the shape of the different spectra could be fit, suggesting that indeed $\tau_i \approx \tau_p$. However, for the experiment at T=23° C., the condition $\omega\tau \gg 1$ prevails and the behavior is mainly elastic. Therefore, the results are not sensitive to the exact value of $\tau$ which mostly affects the amplitude of the spectra and not so much the overall shape, such as position of resonances. In order to investigate this, experiments at temperatures up to T≈50° C. were performed, where the attenuation became large as well as impaired signal to noise ratio. Results showed that $\bar{S}_p$ remained essentially constant in the whole temperature range which again leads to $\neq_i \approx \tau_p$ for the materials used. Indeed $\tau_i$ for the interface material and $\tau_p$ for the amorphous material between the crystalline lamellae in the bulk polymer have the same origin, in that both relate to the mobility of confined PP molecules. All of the data could be described with $\bar{S}_P = \bar{S}_S$. In the present case where $\omega\tau \gg 1$, one may write $L_i'/\mu_i' = L_p'/\mu_p'$ for the elastic part of the modulus and using the relationship $L'/\mu' = 2(1-v)/(1-2v)$ for Poisson's ratio, v, one finds v=0.46. This value is very close to the limit v=0.5 for rubbers and liquids. Results therefore indicate that the interface layer is rubber-like rather than solid-like, in concordance with theoretical predictions and other experiments. It may be said that due to the random nature of the structure, the details for the small molecular movements appear to remain essentially the same for longitudinal and shear waves.

At this point the elastic properties of the interface layer per se may be evaluated. Ultrasonic measurements provide average properties, and therefore the specific stiffness parameter, $S = M_i^*/d_i$ is a mean field quantity, or effective parameter. In the model, $M_i^*$ and $d_i$ can not be considered independently as if the interfacial region had a given modulus and a given thickness. In fact the material that makes up the interface region is not expected to be homogeneous and its modulus may be different, depending on the distance from the substrate. Indeed at the interface, the modulus reflects the strong chemical bonding of the MAG moieties but also the small number of molecules. In the first layer, the structure is dominated by the monomer-substrate interactions that may be attractive or repulsive. Further away from the interface an entanglement network forms with increased rigidity until eventually the final structure of the bulk polymer develops. As may be seen in FIG. 3b, when $\bar{S}_P > 100$, bonding conditions rapidly tend to become rigid-like, which corresponds to the case where $M_i^* \approx M_p^*$. With $d_p = 80$ μm, one finds $d_i \approx 1$ μm for the thickness of this "almost rigid" interface layer. Although this value is not universal, it serves to establish a length scale for the adhesion problem. Since $\omega\tau \gg 1$, one may assume that $\bar{S}_P$ is mostly elastic. Then, starting from $\bar{S}_P \approx (d_p/L_p')(L_i'/d_i) \approx 8.0$ for strong adhesion and with $d_p = 80$ μm and $L_p' \approx 7.0$ GPa, the specific stiffness for the interface layer is $L_i'/d_i \approx 7.0 \times 10^{14}$ N/m³. In relating to polymers and polymer interfaces, the coherence length given by $R_g$ constitutes the natural length scale. Also, here $R_g \approx 10$ nm is of the same order as the thickness of the residual polypropylene films on the anodized substrates after delamination. Taking $d_i \approx R_g \approx 10$ nm, one obtains 7.0 MPa. Proceeding likewise for shear behavior leads to $\mu_i' \approx 2.0$ MPa. For the case of weak adhesion where $\bar{S}_P \approx 2.0$, one finds $L_i'/d_i \approx 1.5 \ 10^{14}$ N/m³, $L_i' \approx 1.5$ MPa, and $\mu_i' \approx 0.5$ MPa. All of the above estimates represent very small moduli, but remain within realistic bounds. Indeed, the smaller modulus, $L_i' \approx 1.5$ MPa is still larger, by two orders of magnitude, than the van der Waals level which constitutes a lower limit for adhesion as long as perfect contact is maintained. Also it is instructive to compare the acoustic modulus with measurements with SFA. In dynamic experiments on low molecular weight melts with no entanglements and no chemical bonding to containing walls, the elastic shear modulus was in the order of MPa. From static measurements on polymer solutions, one may evaluate a longitudinal modulus that is also in the MPa range, corresponding to the minimum in the surface energy curve. Finally from results for the solid surface energy of polymer films one estimates a modulus that also is in the range of MPa. Although these different results are not directly related to our problem, they yield orders of magnitude for the forces in confined molecular systems and are comparable to our measurements.

Examination of the fracture profiles suggested that delamination was initiated in the region $d_i \approx R_g$. With, the hypothesis that failure was mainly due to chain pullout, it was speculated that the level of strain in this region was of the order $\epsilon \approx 1$. Then, using the approximation that the modulus $L_i$ remained constant during fracture, the accompanying stresses were $L_i \epsilon \approx 7$ MPa for the sample with anodized substrates and $L_i \epsilon \approx 1.5$ MPa for the sample with cleansed only substrates. It is noteworthy that these approximations are the same order of magnitude as the nonreversible values measured in practical adhesion, $\sigma_c(\text{an}) \approx 13$ MPa and $\sigma_c(\text{cl}) \approx 6$ MPa. Furthermore, if one assumes that the modulus increases with the number density of grafted chains, $\Sigma$, the ratios $L_i'(\text{an})/L_p' \approx 10^{-3}$ and $L_i'(\text{cl})/L_p' \approx 2.5 \ 10^{-4}$ for samples with anodized and cleansed only substrates suggest that only a small number of chains participate in adhesion. Also, the rather small values of the ratios $L_i'(\text{an})/L_i'(\text{cl}) \approx 4.0$ and $\sigma_c(\text{an})/\sigma_c(\text{cl}) \approx 2.0$ indicate that anodization has only limited influence on adhesion. In principle, one expects that anodizing the substrates would greatly increase the number of grafting sites and that adhesion would be enhanced accordingly. It could be that many of these sites are occupied by short MAG macromolecules with no entanglement coupling to the bulk material. These short chains would not partake in the acoustic modulus nor in practical adhesion. Alternatively, samples with cleansed only substrates in FIG. 9a appeared to lack homogeneity, which could be an indication of internal stresses, or stress concentration originating from poor wetting during fabrication. For our samples, adhesion depends on the possibility of molecules being grafted on the substrates. In turn the degree of grafting is controlled through chemical action on the metal surfaces. Since all other materials characteristics stay constant, changes in adhesion are governed by the properties of the interfacial zone. For the curing of epoxies the problem is somewhat different and more complicated since most materials properties, such as z and also $M_0$ and $M_\infty$, depend on the advancement of polymerization.

A nondestructive method for measuring reversible interfacial adhesion forces has been described. The method is based on mapping data from ultrasonic measurements onto results from a newly developed model for acoustic waves in multilayered media. This mapping is performed by comparing the spectrum from a ultrasonic signal applied to a multilayer composite with a plurality of modeled spectra each having an associated value of S relating to adhesion. A single modeled spectrum is selected on the basis that a best fit or match is found; its corresponding value of S which most closely characterizes the adhesion between the multilayers is determined. Recent ideas concerning the different properties of polymers near surfaces were incorporated and allowance was made for a thin viscoelastic interface layer having a complex modulus $M_i^*$ and a thickness $d_i$. Numerical simulations showed that the system behaved much like an interferometer for the acoustic waves, manifesting high sensitivity to interfacial properties. Concurrently, it was shown that the reflectivity and transmissivity of the bonded structure could be described in terms of the specific stiffness of the interface material, $S=M_i^*/d_i$. Using controlled ultrasonic techniques, the method was demonstrated through experiments on steel/polypropylene/steel samples. Interfacial adhesion was modified by radical grafting of ester and epoxy groups on the polymer and by anodizing the substrates, thereby adding polar species to the metal surfaces. Anodization enhanced the breaking strength in tests for practical adhesion and also the specific stiffness S measured by ultrasonics. Relaxation time in the interfacial region was similar to that of the amorphous component in the semicrystalline material, representative of confined molecules. Also results showed that adhesion is related to elongational forces and not only to shear behavior. Assuming that the thickness for the bonding layer was of the order of the radius of gyration, $d_i \approx R_g$, the ultrasonic modulus was in the range of a few MPa, in agreement with results from other techniques.

With regards to applications in nondestructive evaluation, the method has been used successfully for the characterization of adhesive seals in the food packaging industry. In this case, where the problem was related to polymer/polymer adhesion, it was found that S was directly correlated to processing parameters, namely time, pressure and temperature. All our results point out that the specific stiffness, S, refers to basic materials properties.

TABLE I

| | Density, $\rho$ kg/m³ | Velocity Longitudinal $c_P$ m/s | Velocity Shear $c_S$ m/s | Attenuation Longitudinal $a_P$ m⁻¹ | Attenuation Shear $a_S$ m⁻¹ |
|---|---|---|---|---|---|
| Water | 1000 | 1485 | — | $\approx 0$ | — |
| Steel | 7930 | 5765 | 3084 | $9\ 10^{-14}\ f^2$ | $2.5\ 10^{-13}\ f^2$ |
| PP relaxed | 926 | 1394 | 23 | $\tau = 500$ ns | |
| PP unrelaxed | " | 2851 | 1469 | | |

| | Density, $\rho$ kg/m³ | Real Modulus Longitudinal $L'$ GPa | Real Modulus Shear $\mu'$ GPa | Loss Modulus Longitudinal $L''$ GPa | Loss Modulus Shear $\mu''$ GPa |
|---|---|---|---|---|---|
| Water | 1000 | 2.20 | — | $\approx 0$ | — |
| Steel | 7930 | 263.6 | 75.42 | $43.5\ 10^{-9}\ f$ | $18.52\ 10^{-9}\ f$ |
| PP relaxed | 926 | 1.80 | $0.5\ 10^{-3}$ | $\tau = 500$ ns | |
| PP unrelaxed | " | 7.53 | 2.00 | | |

TABLE I
What we claim is:

1. A method of characterizing interfacial adhesion strength between layers in a multilayer composite having at least three layers, comprising the steps of:
   a) irradiating the multilayer composite with an ultrasonic pulsed signal for interaction therewith, the duration of a pulse of the ultrasonic pulsed signal being approximately less than or equal to 100 nanosecond, to obtain an interaction signal characteristic of the interfacial adhesion strength at the interface of the at least three layers;
   b) detecting the interaction signal from the irradiated multilayer composite;
   c) storing amplitude and phase information corresponding to the detected interaction signal;
   d) convening the stored amplitude and phase information from the time domain to the frequency domain to obtain a frequency spectrum related to the stored information;
   e) comparing the frequency spectrum with a spectrum derived from a model of a multilayer composite that includes at least two additional layers that model the interfacial adhesion strength of the interface between the composite layers, the at least two additional layers including viscoelastic properties expressed in terms of a complex modulus $M_i^*$; and
   f) obtaining a viscoelastic stiffness value characteristic of interfacial adhesion strength between layers of the composite from the model of the multilayer composite having a spectrum that most closely matches the spectrum of the detected interaction signal, the at least two additional layers each having a thickness $d_i$, and whereby the viscoelastic stiffness value is characterized by a parameter $S=M_i^*/d_i$.

2. A method as defined in claim 1, wherein the ultrasonic pulsed signal is comprised of a plurality of pulses and wherein the duration of time between a first and second pulse is at least sufficient to allow the detection of any reverberations that are produced from the first pulse before the occurrence of the second pulse.

3. A method as defined in claim 2, wherein the time interval between pulses is greater than 0.1 millisecond.

4. A method as defined in claim 3, wherein the composite is a metal-polymer-metal multilayer.

5. A method of characterizing interfacial adhesion strength between layers of a multilayer composite comprising the steps of:
   a) ultrasonically irradiating the multilayer composite having at least 3 layers to obtain a first signal characteristic of the interfacial adhesion strength between the at least 3 layers;
   b) modeling the multilayer composite with a model that includes at least two additional layers which model the behavior of the interface between the composite layers in such a manner as to obtain plurality of frequency spectra, each frequency spectrum of said plurality of frequency spectra being characteristic of interfacial adhesion strength between the layers of the modeled multilayer composite;
   c) comparing in the frequency domain, the first signal characteristic of the interfacial adhesion strength between the multilayers with a plurality of the frequency spectra obtained in step (b) to obtain a best frequency spectrum that most closely matches the spectrum of the first signal; and d) determining a value related to the best frequency spectrum obtained in step (c), the value being an indicator of the interfacial adhesion strength in the multilayer composite, the value corresponding to a modulus of the at least two additional layers divided by a thickness of the two additional layers, the multilayer composite being a metal polymer metal composite.

* * * * *